(12) United States Patent
Titmas

(10) Patent No.: US 6,716,360 B2
(45) Date of Patent: Apr. 6, 2004

(54) METHOD AND APPARATUS FOR TREATING WASTE STREAMS

(75) Inventor: James A. Titmas, Akron, OH (US)

(73) Assignee: Eau-Viron Incorporated, Hudson, OH (US)

(*) Notice: Subject to any disclaimer, the term of this patent is extended or adjusted under 35 U.S.C. 154(b) by 0 days.

(21) Appl. No.: 10/122,695

(22) Filed: Apr. 16, 2002

(65) Prior Publication Data
US 2003/0192834 A1 Oct. 16, 2003

(51) Int. Cl.$^7$ .................................................. C02F 1/72
(52) U.S. Cl. ........................... 210/750; 71/28; 210/752; 210/758; 210/761
(58) Field of Search ............................. 210/750, 752, 210/758, 761, 762; 71/28

(56) References Cited

U.S. PATENT DOCUMENTS

| | | | |
|---|---|---|---|
| 3,449,247 A | 6/1969 | Bauer | 210/63 |
| 3,464,885 A | 9/1969 | Land et al. | 162/17 |
| 3,606,999 A | 9/1971 | Lawless | 23/1 |
| 3,853,759 A | 12/1974 | Titmas | 210/63 |
| 4,272,383 A | 6/1981 | McGrew | 210/741 |
| 4,564,458 A | 1/1986 | Burleson | 210/747 |
| 4,594,164 A | 6/1986 | Titmas | 210/741 |
| 4,699,720 A * | 10/1987 | Harada et al. | 210/762 |
| 4,792,408 A | 12/1988 | Titmas | 210/747 |
| 4,803,054 A | 2/1989 | Sillerud et al. | 422/109 |
| 5,096,599 A * | 3/1992 | Granelli | 210/750 |
| 5,160,581 A | 11/1992 | Titmas | 162/61 |
| 5,190,665 A | 3/1993 | Titmas et al. | 210/743 |
| 5,358,646 A * | 10/1994 | Gloyna et al. | 210/762 |
| 5,711,817 A | 1/1998 | Titmas | 127/37 |
| 5,876,613 A * | 3/1999 | Bonnin et al. | 210/609 |
| 5,879,637 A | 3/1999 | Titmas | 422/129 |

* cited by examiner

Primary Examiner—Peter A. Hruskoci
(74) Attorney, Agent, or Firm—Renner, Kenner, Greive, Bobak, Taylor & Weber

(57) ABSTRACT

A method for treating a waste stream, the method including the steps of providing a waste stream that includes waste solids suspended in water, feeding the waste stream to the top of a hydraulic downdraft column, conducting the waste stream to the bottom of the hydraulic downdraft column, conducting the waste steam to a first reaction zone, introducing nitrogen-containing oxides into the first reaction zone so that the waste stream is contacted with the nitrogen-containing oxides, conducting the waste stream up a hydraulic updraft column into a second reaction zone, where the second reaction zone is configured to provide sufficient time so that a reaction between the nitrogen-containing oxides and waste solids can take place and substantially consume the nitrogen-containing oxides, introducing oxygen gas into the waste steam after the nitrogen-containing oxides are substantially consumed, thereby providing a second reactant that reacts with waste solids suspended within the stream, conducting the stream to the top of the hydraulic updraft column.

20 Claims, 5 Drawing Sheets

METHOD AND APPARATUS FOR TREATING WASTE STREAMS

TECHNICAL FIELD

This invention relates to a process whereby sludge waste product can be converted into useful materials by employing a novel gravity pressure vessel.

BACKGROUND OF THE INVENTION

Gravity pressure vessels have been employed in the treatment of waste streams. Specifically, this treatment has included pyrolysis, sub-critical wet oxidation, supercritical wet oxidation, and acid hydrolysis of waste streams. Where wet oxidation is employed, the treatment may include the complete oxidation of the materials within the waste stream or the controlled or restrained oxidation of these waste materials. In either wet oxidation method, oxygen gas ($O_2$) has been employed as the reactant.

Use of $O_2$ as a reactant within a gravity pressure vessel, however, can be disadvantageous. To begin with, $O_2$ is not a readily available product or byproduct of waste treatment, and therefore the $O_2$ must be obtained, i.e., it must be purchased, which can be costly. The use of $O_2$ as a reactant is also problematic in that it presents safety hazards. For example, where the $O_2$ is introduced into the gravity pressure vessel at or near the top of the reactor, the $O_2$ must be introduced at a pressure that is greater than the pressure at the point of injection at the bottom of the reactor. Within some vessels, this pressure could be as high as 2,000–4,000 psi. Further, where the $O_2$ is added at the top of the reactor, the $O_2$ will heat to temperatures as great as 750° F. as the $O_2$ proceeds to the bottom of the reactor. At these temperatures and pressures, the $O_2$ is extremely reactive and, therefore, in addition to presenting safety problems, may in fact destroy the reactor conduits that deliver the $O_2$ to the bottom of the reactor.

Attempts at solving the problems associated with the use of $O_2$ as a reactant have been proposed. In one instance, the prior art teaches constructing a pump station deep within the strata whereby $O_2$ could be pumped into the reactor at the pressure at the point of entry. This procedure, of course, is costly and prone to mechanical failure.

Other attempts have included proposals to introduce oxygen into the waste stream as the waste stream proceeds down the reactor. This procedure, however, proved to be problematic because the oxidation reaction began as the fluid flowed to the bottom of the reactor and therefore the ability to achieve a peak reaction temperature was hindered. As a result, insufficient degradation of waste products occurred.

In still other applications of wet oxidation, hydrogen peroxide is used as a liquid form of oxygen. Hydrogen peroxide, is several times more expensive than oxygen gas under pressure and the pre-heating of the hydrogen peroxide causes it to decompose, making control of the net injection into a gravity pressure vessel problematic. The use of hydrogen peroxide as an oxidant in wet oxidation is thus limited to small capacity units that employ a pump and reactor tank that does not involve any significant pre-heating of the oxygen feed.

Although numerous problems have ben confronted in the wet oxidation of waste streams within gravity pressure vessels, wet oxidation treatment processes have significant potential for the efficient and environmentally sound treatment of waste streams. Accordingly, there remains a need to improve upon these processes, especially those processes.

SUMMARY OF INVENTION

In general the present invention provides a method for treating a waste stream, the method including the steps of providing a waste stream that includes waste solids suspended in water, feeding the waste stream to the top of a hydraulic downdraft column, conducting the waste stream to the bottom of the hydraulic downdraft column, conducting the waste steam to a first reaction zone, introducing nitrogen-containing oxides into the first reaction zone so that the waste stream is contacted with the nitrogen-containing oxides, conducting the waste stream up a hydraulic updraft column into a second reaction zone, where the second reaction zone is configured to provide sufficient time so that a reaction between the nitrogen-containing oxides and waste solids can take place and substantially consume the nitrogen-containing oxides, introducing oxygen gas into the waste steam after the nitrogen-containing oxides are substantially consumed, thereby providing a second reactant that reacts with waste solids suspended within the stream, conducting the stream to the top of the hydraulic updraft column.

The present invention also includes a wet oxidation process for treating a waste stream of the type that employs a gravity pressure vessel, where the improvement comprises providing oxides of nitrogen to the gravity pressure vessel as an oxidant.

The present invention advantageously overcomes problems associated with the prior art by employing oxides of nitrogen as an additional or alternative oxidant in the wet oxidation of waste streams. The oxides of nitrogen can be added to the reactor in the aqueous state, and by doing so only minimal pressures are required to introduce the oxidant into the reactor. Also, by employing nitrogen oxides, ammonia is provided as a byproduct of the wet oxidation reaction. This ammonia can be advantageously captured and employed as a useful product such as in the production of urea. Alternatively, the ammonia can be converted into oxides of nitrogen and recycled as a reactant in the wet oxidation process. Further, the use of nitrogen containing oxides as an oxidant has led to the unexpected discovery that sub-critical wet oxidation processes can be made more efficient because mass transfer limitations associated with $O_2$ can be minimized or eliminated.

PREFERRED EMBODIMENT FOR CARRYING OUT THE INVENTION

The overall process and apparatus of this invention can be described with reference to FIG. 1. Those skilled in the art appreciate that appropriate pumping devices and conduits can be employed to move material between the various stages of the system and that this process and system can be maintained in a continuous operation.

The preferred material to be treated by the process and apparatus of this invention is the sludge waste byproduct that is produced by municipal waste water treatment plants. These sludges vary in composition based upon the location of the wastewater treatment plant and the time of the year. In general, however, the sludges include from about 1 to about 4.5 weight percent suspended solids, although greater variations may be found in some municipalities. The suspended solids may include, for example, biomass, suspended minerals, detergents, ashes, metal oxides, soil particles, inert materials, sand grains, polymers, food wastes, phosphates, nitrogen, and the like. The waste stream, e.g., sludge, maybe referred to as a raw waste stream.

Figure 1:
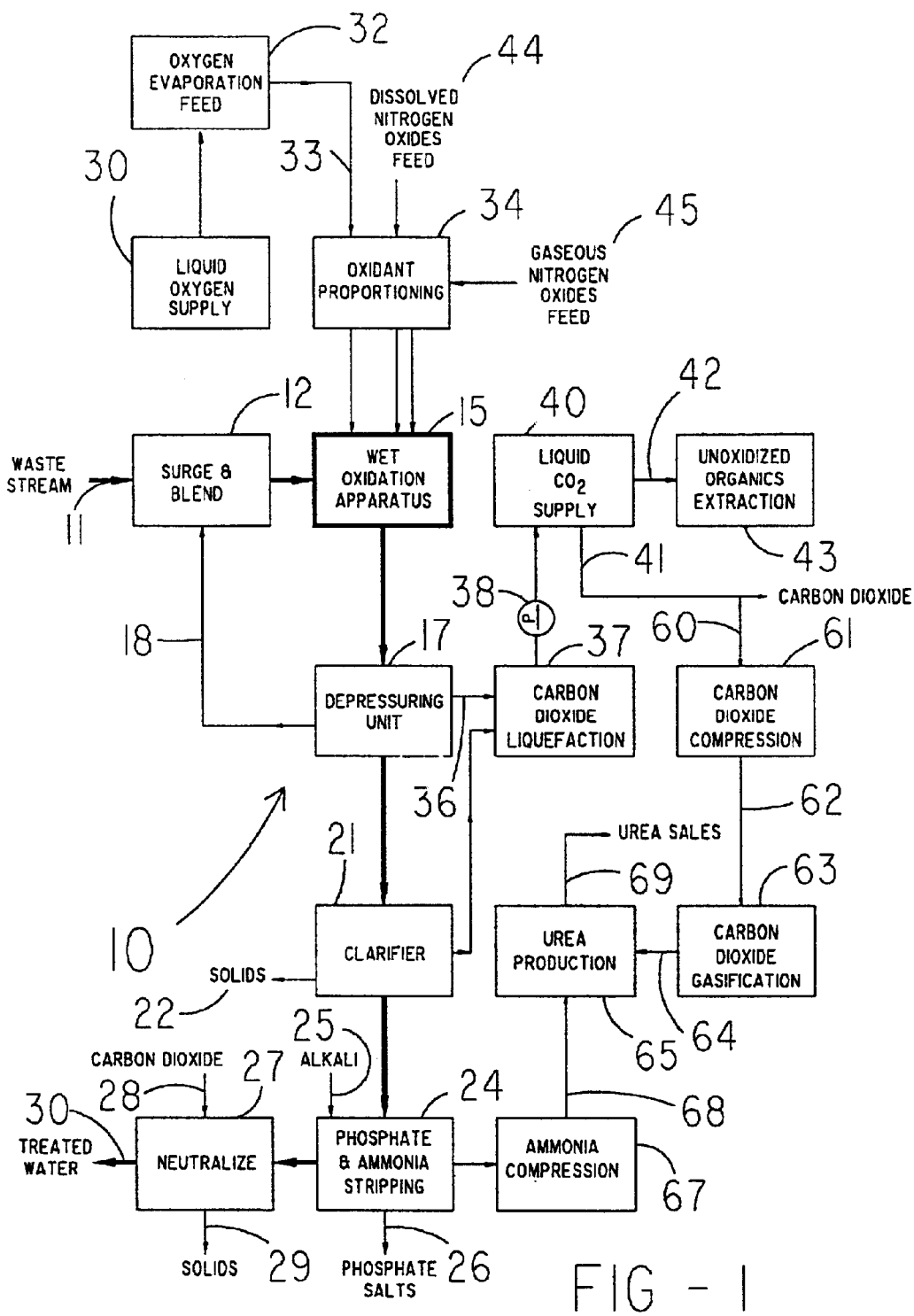
FIG. 1 is a schematic diagram of the overall process and system of th present invention.

With reference to FIG. 1, a raw waste stream 11 is preferably diluted within a surge and blend tank 12. Within tank 12, raw waste stream is preferably diluted to less than about 10% solids, more preferably from about 0.5 to about 5% solids, and even more preferably from about 1 to about 2% by weight suspended solids, i.e., waste materials in water. This diluted stream is then delivered to a wet oxidation apparatus 15, where oxygen and oxides of nitrogen are added as reactants to treat the raw waste stream. As part of this treatment, the oxygen and oxides of nitrogen are intended to provide sufficient oxygen to convert organic matter within the waste stream to carbon dioxide, water, and a few simple organic acids. Also, the oxygen and oxides of nitrogen are intended to fully oxidize entrained metals and convert nitrogen oxides to ammonium ions. Nitrogen oxides may simply be referred to as NOx inasmuch as various oxides of nitrogen may be employed as a reactant.

The products of wet oxidation, which are included in the treated stream after removal from wet oxidation apparatus 15, are preferably separated for recovery. In one embodiment, this can be accomplished by introducing the treated stream into an atmospheric tank 17 where the treated stream is mostly depressurized. A portion of this treated stream can optionally be employed to dilute the raw waste stream 11 by adding it to the surge and blend tank 12 via conduit 18.

Carbon dioxide released as a result of depressurizing the treated liquid stream at tank 17 can be captured and further treated as desired. The remainder of the treated stream can be further processed by, for example, passing the treated stream through a clarifier 21 where precipitated solids can be removed. Additional carbon dioxide can be removed from clarifier 21 and further treated as desired.

Further treatment of the stream can include phosphate and ammonia removal at tank 24. The pH of the treated stream within tank 24 is preferably increased, e.g., above about 8.5 and preferably above 8.9, which thereby causes the precipitation of phosphate salts as solids and the release of ammonia gas. The precipitated phosphate salts can be removed via conduit 26 and further processed as desired. Ammonia gas can likewise be recovered and further processed as desired. In one embodiment, the ammonia can be captured and compressed at compressor 67 and reacted with carbon dioxide to form urea within production tank 69. Preferably, the carbon dioxide is supplied from carbon dioxide that was captured from atmospheric tank 17 and clarifier 21.

The remainder of the treated stream exiting tank 24, from which the ammonia and phosphates have been substantially removed, can then be neutralized to lower the pH (e.g., by adding carbonic acid that can be produced from the carbon dioxide captured from atmospheric tank 17 and clarifier 21).

The neutralized stream, which is substantially free of solid precipitates formed during neutralization and includes from about 300 to about 1,000 ppm of biodegradable dissolved solids, can then be directed toward a wastewater treatment facility.

In one preferred embodiment, the carbon dioxide captured from atmospheric tank 17 and clarifier 21 is further treated. In a first step of this treatment, the carbon dioxide stream is pressurized and cooled (e.g., about 15° C. and about 1,700 MPa) in condenser 37 to liquify the carbon dioxide.

The remainder of the stream may contain residual nitrogen and oxygen gas, which can be collected as a gas or simply liberated to the environment. Volatile organic compounds collected from tank 17 or clarifier 21 treated in condenser 37 are typically precipitated as a semi-solid. This semi-solid can be accumulated and extracted in a batch out-loading process. These extracted semisolids can then be combusted in a combustion chamber (not shown), which typically occurs at temperatures in excess of 3,000° F. by using air supplemented with oxygen to enhance the production of NOx. The gases released from combustion chamber, i.e., exhaust gases, are preferably treated so that the residual acids, such as nitrogen-containing acids, can be condensed and removed from the exhaust. The nitrogen-containing (e.g., NOx) acids recovered from the exhaust stream can then be employed as a reactant within the wet oxidation apparatus 15.

Figure 2:
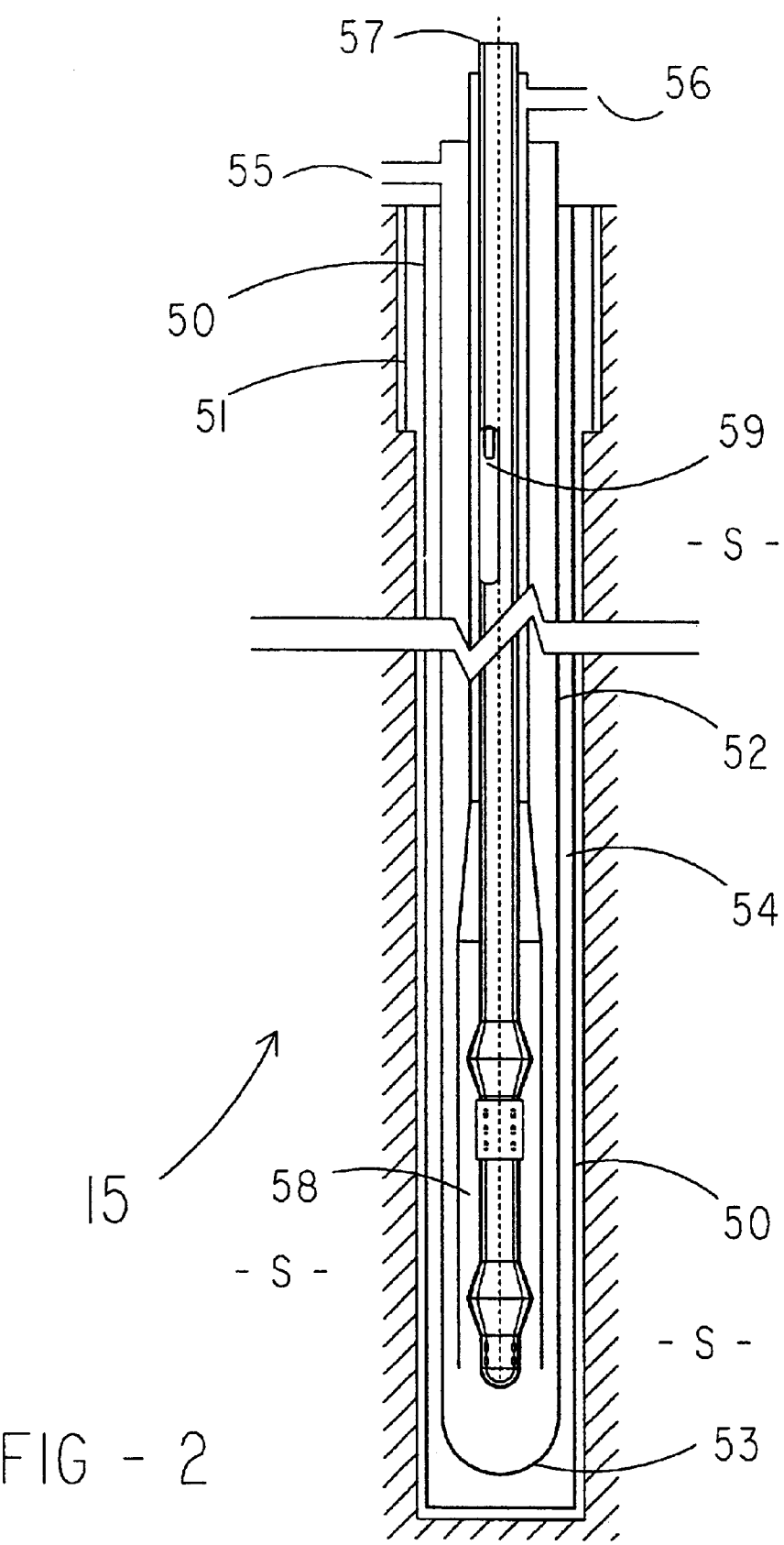
FIG. 2 is a fragmented vertical, cross-sectional view of a gravity pressure vessel in place within the strata.

Wet oxidation apparatus 15 is a gravity pressure vessel, which is best described with reference to FIGS. 2 and 3. A tubular casing 50, which may also be referred to as a long string or containment casing, is positioned in the strata S in a bore within the earth. Casing 50 can be separated from strata S with a grout to control the intermixing of fluids that may be present within strata S, to reduce heat losses from the apparatus, and to protect casing 50 from adverse corrosive effects of strata S. Optionally, a surface casing 51 may be employed, which is an additional tubular member encompassing strata casing 50 for the purpose of protecting water aquifers during drilling of the long-string chamber bore hole.

Concentric within and spaced from casing 50 is an outer vessel wall 52, which has lower closed end 53. The space between casing 50 and outer vessel wall 52 forms an isolating annulus 54 that acts as a mutual barrier to protect strata S from the apparatus and to protect the apparatus from the strata. This isolation may be enhanced by evacuating annulus 54 to a lower pressure, such as to approximately to one-thousandth of an atmosphere. Under these conditions, the integrity of casings 50 and outer vessel wall 52 will be verified and heat loss to the strata from the apparatus will be greatly reduced, as will the corrosive effects on the surface of both casings 50 and outer vessel wall 52.

Figure 3:
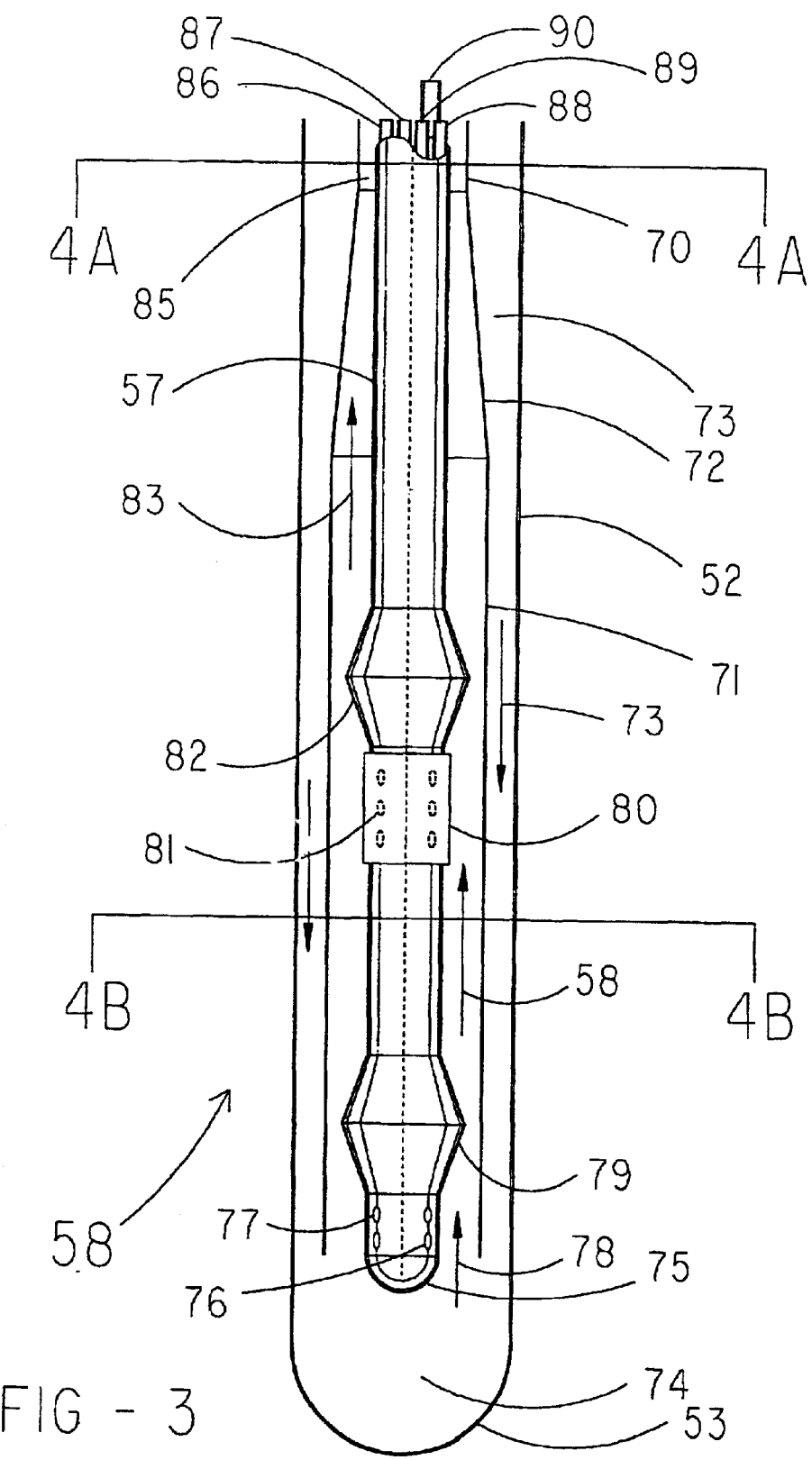
FIG. 3 is a vertical, cross-sectional view of the lower portion of a gravity pressure vessel.

Concentric within and spaced from outer vessel wall 52 is counterflow tubulars 70, 71, and 72, as shown in of FIG. 3, which act as a heat exchanger. The space between outer vessel wall 52 and counterflow tubular 70 forms outer annulus 73, which is essentially a vertical passageway or hydraulic downdraft column that includes inlet 55, as shown in FIG. 2 that receives the stream and delivers the stream to the bottom 74 of vessel 52. Counterflow tubular 70 is preferably made of a material that will conduct heat between outer flow annulus 73 and inner annulus 83, as shown in FIG. 3.

Concentric within and spaced from counterflow tubular 70 is inner-wall tubular 57. The space between inner-wall tubular 57 and counterflow tubular 70 forms inner vessel annulus 83, which defines a second vertical passageway or hydraulic updraft column that includes outlet 56, as shown in FIG. 2.

Figure 4A:
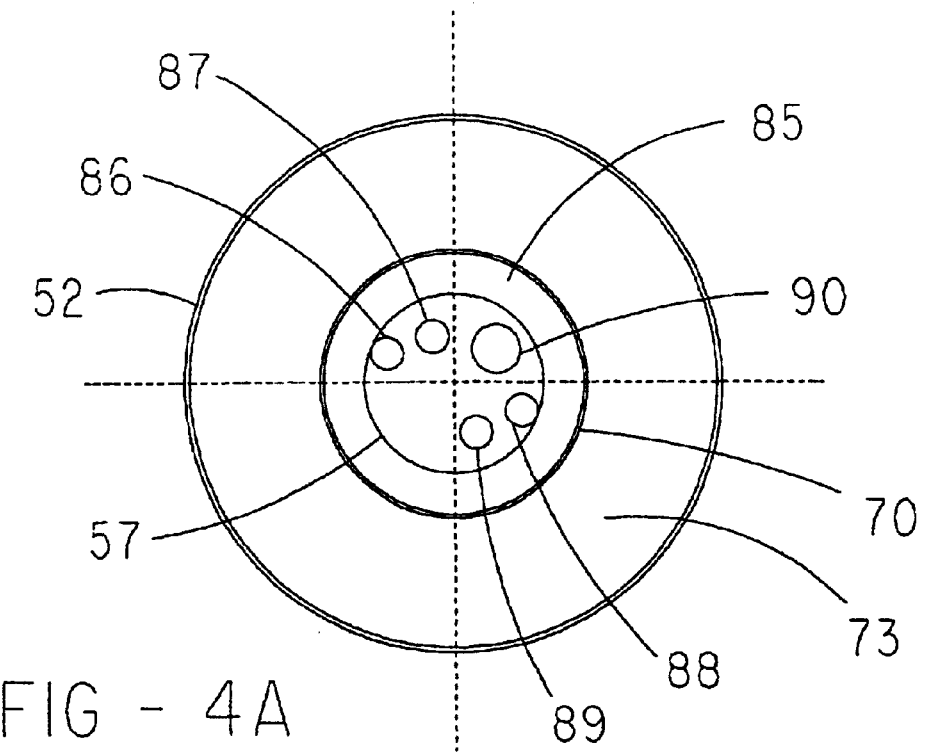
FIGS. 4A and 4B are sectional views taken substantially along 4A—4A and 4B—4B of FIG. 2, respectively.
Figure 4B:
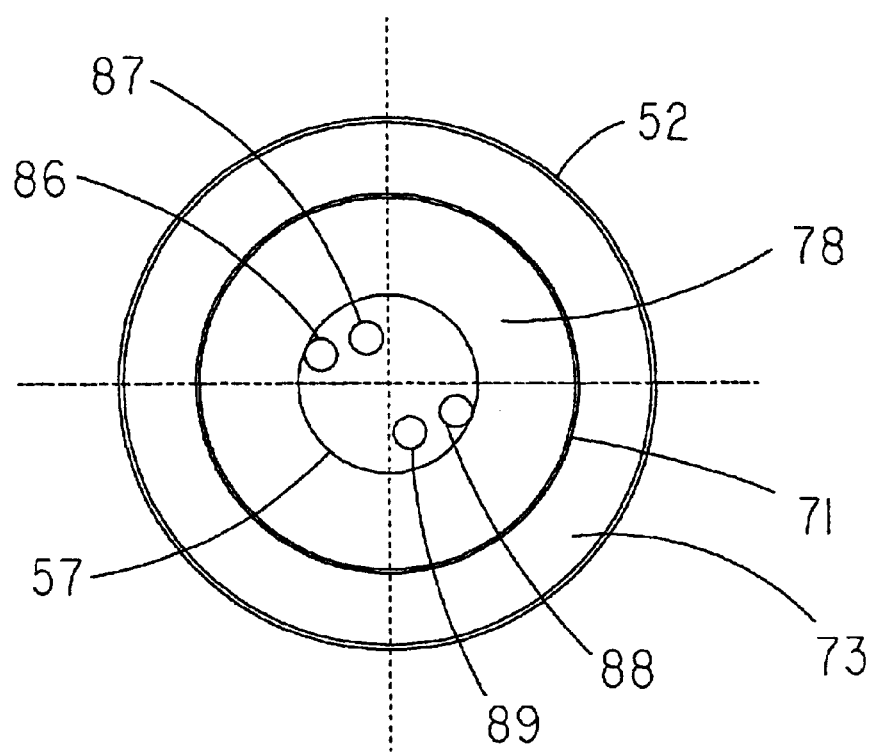
Figure 5:
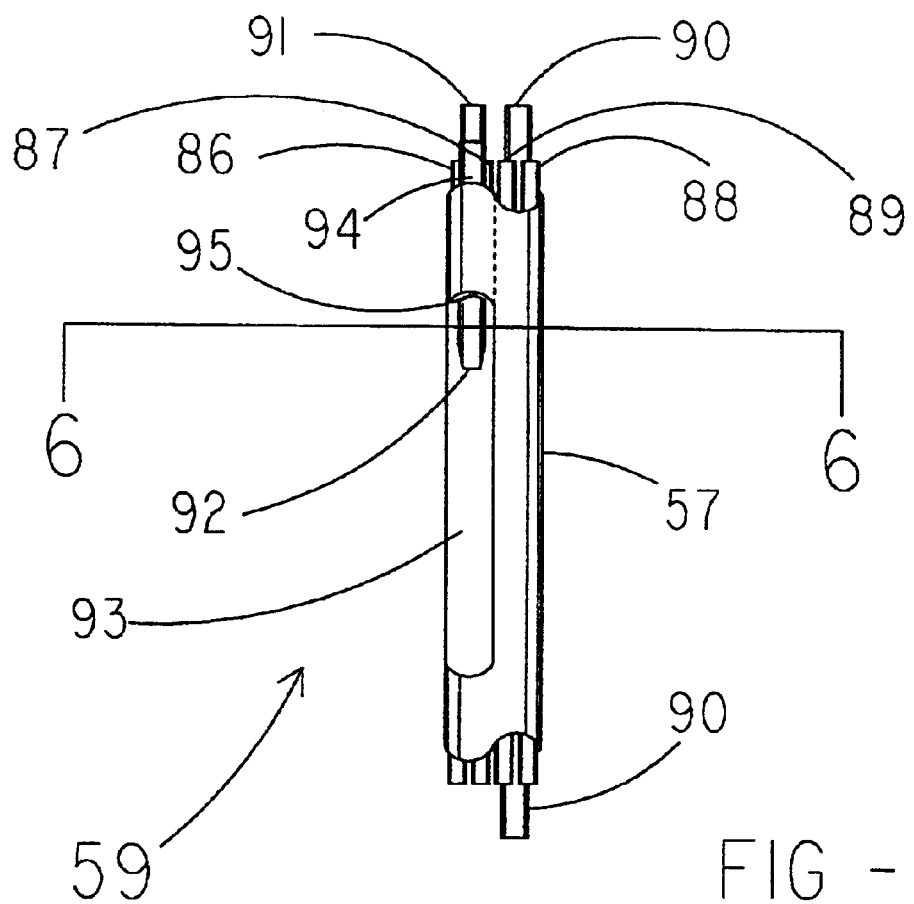
FIG. 5 is a fragmented vertical, cross-sectional view of the tubular casing within the gravity pressure vessel.
Figure 6:
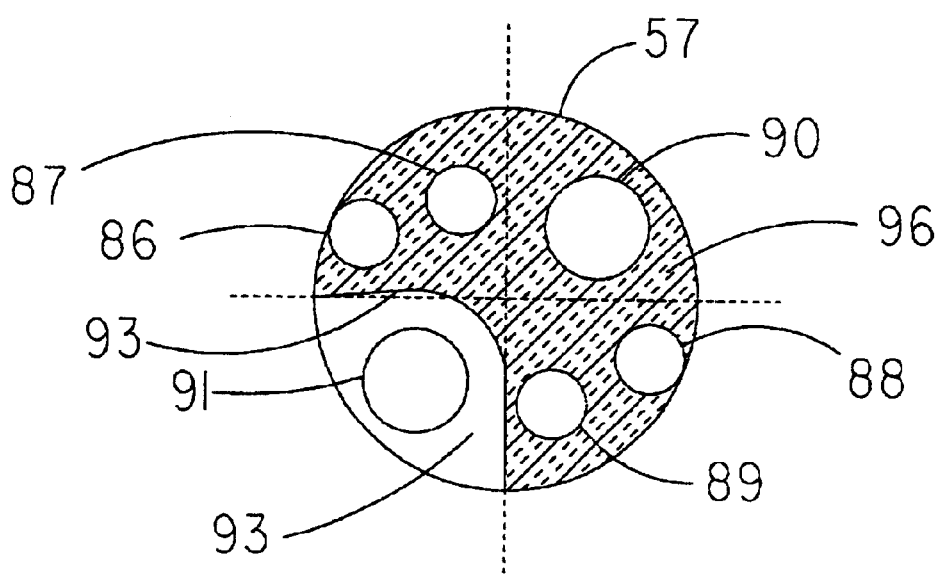
FIG. 6 is a sectional view taken substantially along line 6—6 of FIG. 4.

As shown in FIGS. 4A, 4B, and 5, encased within inner-wall tubular 57 are various feed pipes that can be employed to deliver reactants or energy to various areas within the vessel or to provide conduits for sampling or providing various devices that may be needed to monitor the conditions within the vessel. In a preferred embodiment, the feed pipes include oxygen feed pipe 90, steam feed pipe 91, NOx feed pipe 87, acid feed pipe 88, which can also be employed to deliver catalyst, base feed pipe 89, which can also be employed as a sampling pipe, and thermocouple casing 86. Preferably, steam feed pipe 91 is suspended within indentation pocket 93 of tubular 57, which allows steam feed pipe 91 to thermally expand or contract. The space between steam feed pipe 91 and feed pipe housing 94 forms steam feed annulus 95 in FIG. 5, which could be charged with gas, e.g., nitrogen or air, to prevent waste or wastewater from entering annulus 95. The remainder of the area within inner tubular 57 not occupied by the various feed pipes may be filled with insulation or grout 96 as shown in FIG. 6.

With regard to steam feed pipe 91, it should be understood that steam is advantageously only required during start-up of the vessel. In other words, once the vessel is in operation, the heat generated by the operation of the vessel may sustain its continuous operation without the need for added energy from sources such as steam. In one embodiment, steam feed pipe 91 terminates at indentation 93 within service inner-wall tubular 57, as shown in FIG. 5. The depth at which indentation 93 is located can be selected based upon a number of parameters including the pressure required to deliver steam within the vessel. For example, if the steam is injected at a depth of about 2500 feet, about 1100 psi of pressure may be required to deliver the steam. Or, where the steam is injected at a depth of about 3500 feet, about 1500 psi of pressure may be required to deliver the steam. In another embodiment, which is not shown, the steam may also be introduced into outer vessel annulus 73. This upper delivery may be preferred inasmuch as the steam may be introduced at less depth, and therefore less pressure, with the primary consideration being to achieve a temperature of about 350° F. at the bottom of the reactor, i.e., reaction chamber 58, at that time when the wet oxidation process is first activated.

With reference again to FIG. 3, oxygen feed pipe 90 is attached to and communicates with oxygen diffuser 80. Oxygen diffuser 80 preferably includes a porous ceramic material through which oxygen gas may diffuse. In one embodiment, oxygen diffuser includes an apparatus for effecting a selected pattern of fluid flow, which is disclosed in U.S. Pat. No. 4,874,560, which is incorporated herein by reference. NOx feed pipe is attached to and communicates with NOx outlet 76. Feed pipe 88 and pipe 89 are attached to and communicate with reaction chamber 78 for the purposes described hereinbefore including catalyst injection, sampling or pH adjustment at opening 77.

Inner service tubular 57 includes lower venturi 79 and upper venturi 82. These venturi are positioned along the same vertical axis with respect to the length of the tubular 57. Both venturi 79 and 82 preferably include two oppositely directed frustrums, connected at their bases, that circumscribe inner wall tubular 57. As a result of these venturi, the inner annuli 78 and 58 respectively are reduced at the junctions 79 and 82 of the two bases. Venturi 79 and 82 alter the flow rate of the fluid as it travels up annulus 83, and thereby serve to mix the fluid. Also, venturi 79 and 82 serve to define various reaction areas within gravity pressure vessel 50. Specifically, the area below lower venturi 79 near bottom 74 of vessel 52 defines a first reaction zone 78. The area between lower venturi 79 and upper venturi 82 defines a second reaction zone 58. The area above upper venturi 82 defines a third reaction zone within inner annulus 83. The desired reactions are deliberately allowed to go to an end point without quenching. As a result, the reaction will continue throughout updraft annulus 85 to the ground surface.

As shown if FIG. 3, counterflow tubulars, 70, 71, and 72 preferably includes an upper section 70, a lower section 71, and a baffle enlargement 72 between the upper section 70 and lower section 71. Upper section 70 has a narrower diameter than lower section 71. As a result of this configuration, inner updraft annulus 85 has less overall area above baffle 72, and outer annulus 73 has a greater overall area above baffle 72. Likewise, inner annulus 83, 58 and 78 have a greater overall area below baffle 71, and outer annulus 73 has less overall area below baffle 71.

During normal operation of gravity pressure vessel 52, the waste stream enters vessel 52 at inlet 55 where wastes suspended in water are caused to descend to a zone of higher pressure within outer vertical annulus 73. This pressure results from the cumulative weight of the stream, as well as from residual pressures from fluid handling pumps, which might be utilized (not shown). This stream will be heated by the fluid stream traveling up annulus 85 via heat recovered through counterflow heat exchange tubular 70. By preheating the waste stream, the viscosity of the stream will be decreased and thereby facilitate the passage of the stream past baffle 72 into the area of annulus 73 where the overall area is restricted.

When the stream reaches first reaction zone 78, which is proximate to bottom 74 of service tubular 71, the stream is contacted with aqueous NOx that is introduced via feed port 76 and may be supplemented via feed introduced into first reaction zone 78 via feed port 77. Preferably, the pH of the stream is adjusted to a pH of about 7.5 to about 8.0 as may be desired to accommodate a particular chemical reaction. This may not be required because the pH of the incoming waste stream can likewise be adjusted within surge and blend tank 12 prior to entry into vessel 52.

By contacting the waste stream and aqueous NOx, wet oxidation of the wastes within the waste stream is intended to begin within first reaction zone 78. The stream, which may now contain reacted NOx and wastes, continues up inner annulus 78 where it contacts lower venturi 79, which induces mixing. Past lower venturi 79, the stream enters second reaction zone 58. The length of this reaction area is preferably configured so that the reaction between the oxygen provided by the NOx and the wastes within the stream is substantially completed. In preferred embodiments, where lower venturi 79 simply provides passive mixing of the waste stream, the length of second reaction zone 79 is preferably configured to provide a reaction time of about 3 to about 6 minutes.

The stream is then contacted with oxygen that is released into the second reaction zone 58 via diffusor 80. Preferably, the oxygen is introduced into the second reaction zone 58 at a location near upper venturi 82 so that the oxygen contacts the stream immediately prior to the stream contacting upper venturi 82. Upper venturi 82 induces mixing of the stream as the stream enters third reaction zone 83. Third reaction zone 83 is configured so as to allow adequate reaction time to complete the oxidation of any organic debris that may be included in the waste stream. As those skilled in the art will appreciate, this reaction time should preferably account for the mass transfer required to dissolve the oxygen that is suspended in the stream. Once dissolved, the reaction between the oxygen and the organic debris within the waste stream is believed to be nearly instantaneous.

As the stream proceeds through third reaction zone 83, it is believed that oxides of nitrogen and other nitrogen-containing compounds within the waste stream react with hydrogen from the organic debris to form ammonium ions and carbon dioxide. The oxygen can react with the organic debris or serve to oxidize metals to their highest oxidation state, which for most metals will result in a metal oxide precipitate. Once the stream proceeds through third reaction zone 83, the stream will contact baffle 72, where the area within inner reactor annulus 85 will be reduced. The length of inner reaction annulus 85 above baffle 72 is preferably selected, by selecting the overall length of the vessel 52, so as to dissipate pressure within the reactor that is generated by the convective forces resulting from the difference between the overall density of the downdrafting and updrafting fluids.

As noted above, the processes of the present invention are particularly advantageous when operating at sub-critical wet oxidation conditions. For purposes of this specification, sub-critical wet oxidation processes include those processes that are conducted at temperatures of about 550° to about 705° F. (preferably up to about 680° F.) and pressures of about 800 to about 3,000 psi (preferably about 1,800 to about 2,700 psi). While the preferred embodiments of this invention are directed toward sub-critical wet oxidation processes, the practice of this invention is also useful at supercritical wet oxidation processes, which typically are conducted at temperatures and pressures in excess of those conditions experienced in sub-critical wet oxidation processes.

While the best mode and preferred embodiment of the invention have been set forth in accord with the Patent Statues, the scope of this invention is not limited thereto, but rather is defined by the attached claims. Thus, the scope of the invention includes all modifications and variations that may fall within the scope of the claims.

What is claimed is:

1. A method for treating a waste stream, the method including the steps of:
    providing a waste stream that includes waste solids suspended in water;
    feeding the waste stream to the top of a hydraulic downdraft column;
    conducting the waste stream to the bottom of the hydraulic downdraft column;
    conducting the waste steam to a first reaction zone;
    introducing nitrogen-containing oxides into the first reaction zone so that the waste stream is contacted with the nitrogen-containing oxides;
    conducting the waste stream up a hydraulic updraft column into a second reaction zone, where the second reaction zone is configured to provide sufficient time so that a reaction between the nitrogen-containing oxides and waste solids can take place and substantially consume the nitrogen-containing oxides;
    introducing oxygen gas into the waste stream after the nitrogen-containing oxides are substantially consumed, thereby providing a second reactant that reacts with waste solids suspended within the stream;
    conducting the stream to the top of the hydraulic updraft column where the step of introducing nitrogen-containing oxides results in the formation of ammonium ions, and where said ammonium ions are recovered from the stream after the stream is conducted to the top of the hydraulic updraft column.

2. The method of claim 1, where heat resulting from the reactions between the waste solids and the nitrogen-containing oxides or the oxygen is transferred from the hydraulic updraft column to the hydraulic downdraft column.

3. The method of claim 1, where the hydraulic downdraft column has a greater area at the top of the column than at the bottom of the column.

4. The method of claim 1, where the pressure experienced by the waste stream at the bottom of the hydraulic updraft column is about 1,800 to about 2,700 psi.

5. The method of claim 4, where the temperature of the waste stream at the bottom of the hydraulic updraft column is about 550 to about 680° F.

6. The method of claim 1, where the volume of the hydraulic updraft column within first reaction zone is maximized so as to facilitate the reaction between the nitrogen-containing oxides and the waste solids within the stream.

7. The method of claim 1, where the ammonium ions is reacted with carbon dioxide to form urea.

8. The method of claim 1, where the step of introducing nitrogen-containing oxides results in the formation of carbon dioxide, and where said carbon dioxide is recovered from the stream after the stream is conducted to the top of the hydraulic updraft column.

9. The method of claim 8, where the carbon dioxide is reacted with ammonium ions to form urea.

10. The method of claim 1, where steam is introduced into the hydraulic updraft column above the second reaction zone, and where the steam is introduced at a pressure that is less than pressure experienced at the bottom of the hydraulic downdraft column.

11. The method of claim 1, where the cross-sectional area of the hydraulic downdraft column decreases from the top of the column to the bottom of the column and where the cross-sectional area of the hydraulic updraft column increases from the top of the column to the bottom of the column.

12. The method of claim 1, where during said step of conducting the waste stream of a hydraulic updraft column into a second reaction zone includes passively mixing the waste stream.

13. The method of claim 12, where said second reaction zone is configured to provide a reaction time of about 3 to about 6 minutes.

14. The method of claim 1, where the nitrogen-containing oxides are introduced in an aqueous solution.

15. A wet oxidation process for treating a waste stream including waste solids suspended in water of the type that employs a gravity pressure vessel, where the improvement comprises providing an aqueous solution including oxides of nitrogen to the gravity pressure vessel as an oxidant so that a reaction between the oxides of nitrogen and the waste solids take place and substantially consumes the oxides of nitrogen resulting in the formation of ammonium ions, and said ammonium ions are recovered from the stream.

16. The process of claim 15, where the conditions within the gravity pressure vessel include sub-critical conditions.

17. The process of claim 16, where a further improvement comprises adding oxygen gas to the reactor once the oxides of nitrogen have been substantially reacted.

18. The process of claim 15, where a further improvement comprises employing a gravity pressure vessel that includes a first reaction zone at or near the bottom of the reactor, where the oxides of nitrogen are introduced in the first reaction zone.

19. The process of claim 18, where a further improvement comprises employing a gravity pressure vessel that includes a second reaction zone, where the length of the second reaction zone is sufficient to allow the oxides of nitrogen to substantially react with solids within the waste stream, and where oxygen is introduced into the second reaction zone at the end of the zone.

20. The process of claim 19, where a further improvement comprises defining the second reaction zone by a lower venturi that restricts flow of the waste stream as it enters the second reaction zone and an upper reaction that restricts flow of the waste stream as it exits the second reaction zone.

* * * * *